Figure 5D:
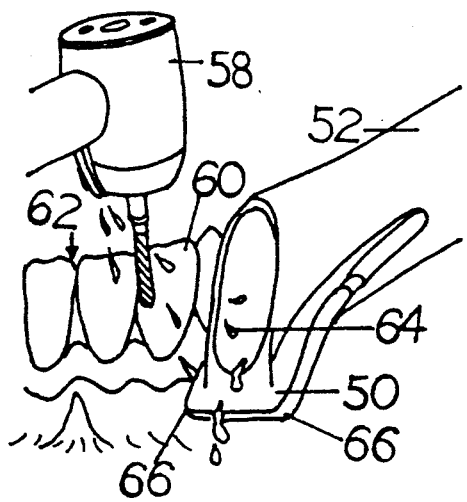

United States Patent [19]

Young et al.

[11] Patent Number: 5,165,891
[45] Date of Patent: Nov. 24, 1992

[54] HIGH-VOLUME EJECTOR WITH VALVES AND SPACING FIN

[76] Inventors: Rily Young, 8681 Luss Dr., Huntington Beach, Calif. 92646; James Shen, 18751 Beach Blvd., Huntington Beach, Calif. 92648

[21] Appl. No.: 644,073

[22] Filed: Jan. 18, 1991

[51] Int. Cl.⁵ .......................... A61C 17/06; F16K 1/22
[52] U.S. Cl. ......................................... 433/95; 433/93; 251/297; 251/305; 604/902
[58] Field of Search ...................... 433/91, 93, 95, 96; 604/33, 118, 902; 251/297, 305, 308, 339; 137/527, 852

[56] References Cited

U.S. PATENT DOCUMENTS

| | | | |
|---|---|---|---|
| 2,662,545 | 12/1953 | Kelley | 251/339 |
| 2,815,924 | 12/1957 | Burch | 251/305 |
| 3,299,511 | 1/1967 | Hutson | 433/96 |
| 3,904,173 | 9/1975 | Naylor | 251/308 X |
| 4,049,000 | 9/1977 | Williams | 433/95 X |
| 4,194,722 | 3/1980 | Okerblom | 251/305 |

FOREIGN PATENT DOCUMENTS

| | | | |
|---|---|---|---|
| 3032522 | 4/1982 | Fed. Rep. of Germany | 433/91 |
| 0103170 | 8/1980 | Japan | 137/852 |
| 0009376 | 1/1984 | Japan | 251/305 |
| 165434 | 11/1933 | Switzerland | 251/308 |
| 2011586 | 7/1979 | United Kingdom | 251/305 |

*Primary Examiner*—Robert P. Swiatek
*Assistant Examiner*—Nicholas D. Lucchesi
*Attorney, Agent, or Firm*—David Pressman

[57] ABSTRACT

A saliva ejector for dental use comprises a tube (16) having an open end with a slanted edge (32) and a tip valve comprising a disc (22) and a pivot attachments (24) mounted adjacent the tip. The valve enables the tube to be closed without having to touch any non-sterilizable parts, thereby avoiding cross-contamination of patients with microorganisms. The pivot attachments are integral with the wall of the tube, but can be pivoted in pivot holes (36) therein. A pair of operating arms (28) are attached normal to the disc so that the valve can be closed from the open end of the tube by pulling the arm down with a finger; the arms also provide the valves with an inherent screen-filter. A notch (12) in the open end of the tube receives and holds the arm when the valve is closed. The tip of the tube can have a spacing fin (72) attached. The fin has rounded side edges and a front blunt point (74) and is at a narrower angle to the axis of the tube than the slanted open end thereof so as to cross said open end and thereby avoid intefering with dental work. For finned tubes, a valve (84) is provided in an intermediate position in the tube. This valve comprises a pivotable plate (86) on an arm (88) which extends to an operating handle (80) on the outside of the tube. The arm is initially integrally attached to the wall of the tube by frangible webs (96), but these are broken the first time the handle is turned so as to provide pivot holes (96') in the wall. The plate has projecting normal arms (94) to provide an inherent screen-filter.

20 Claims, 4 Drawing Sheets

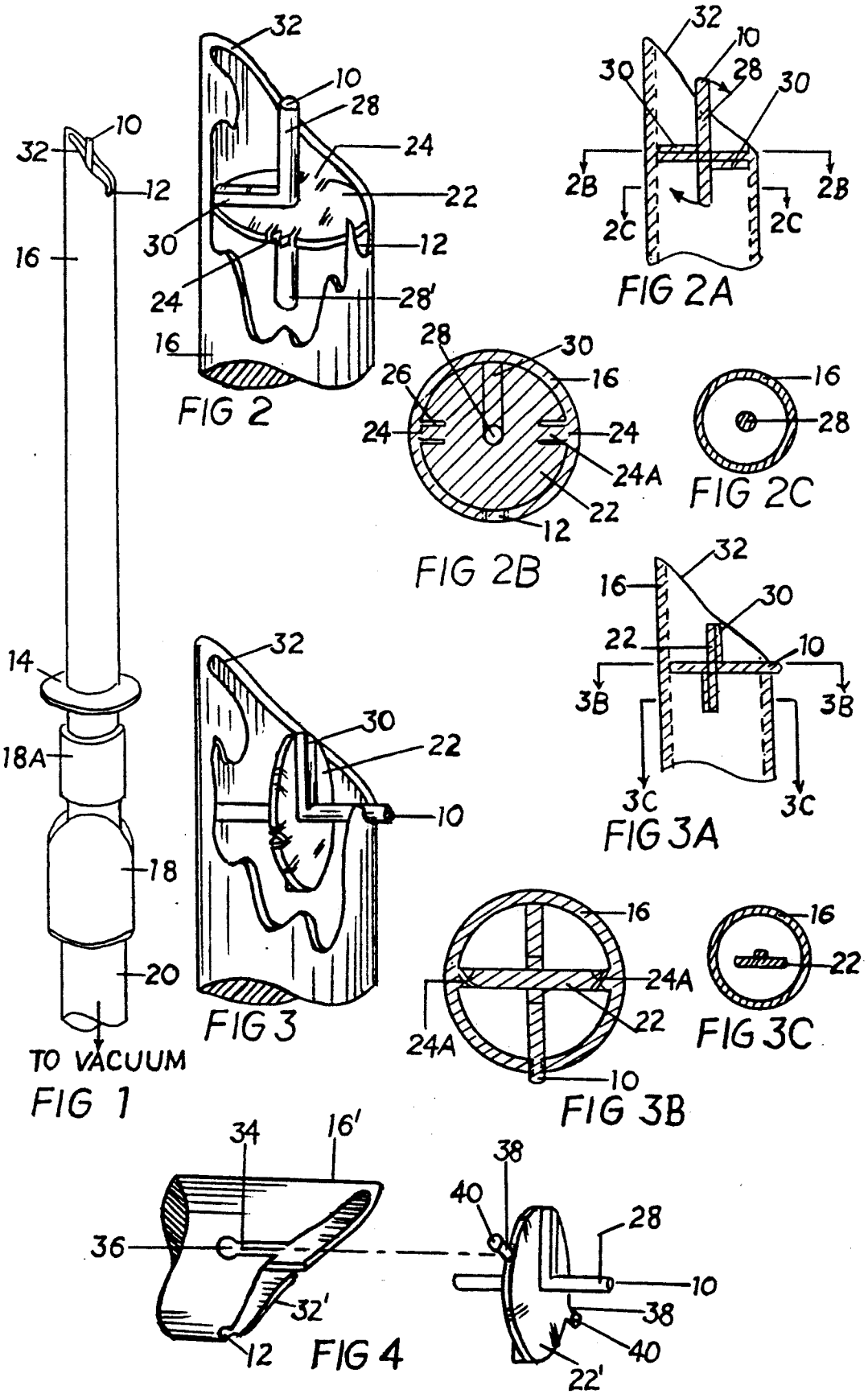

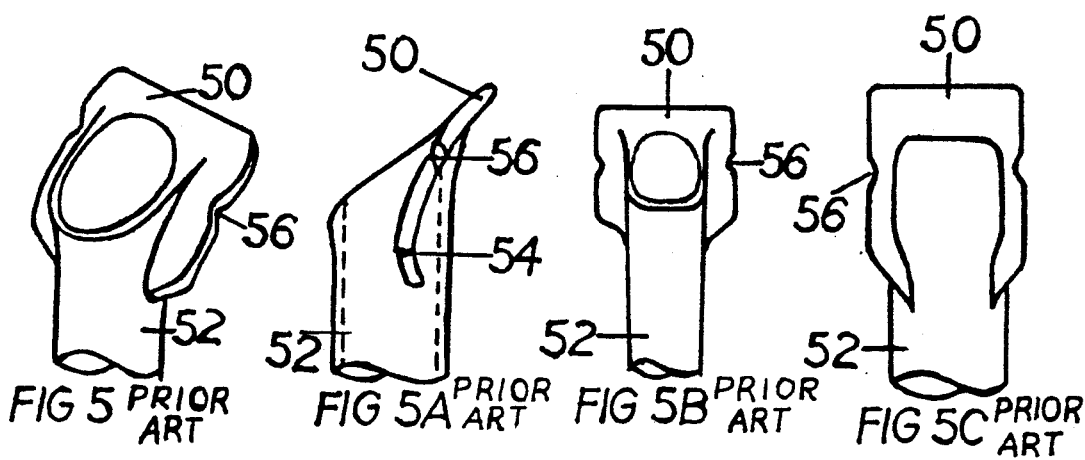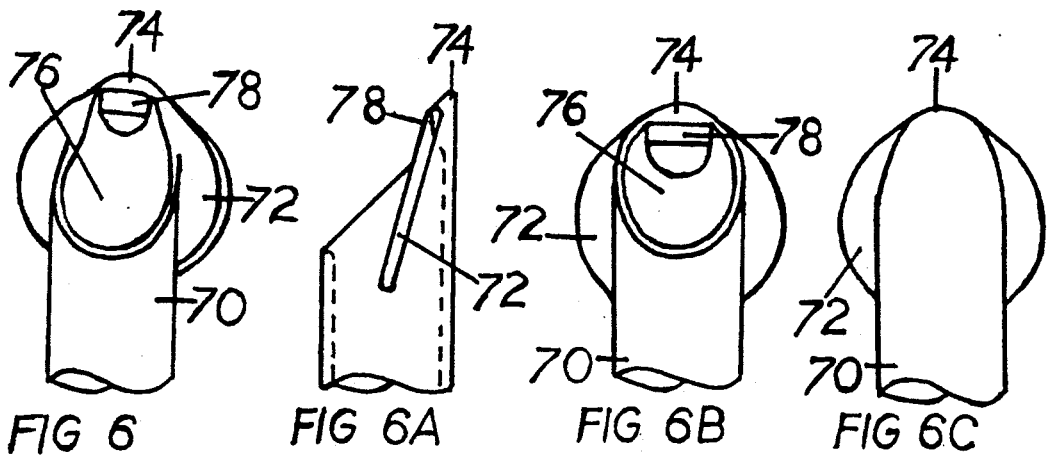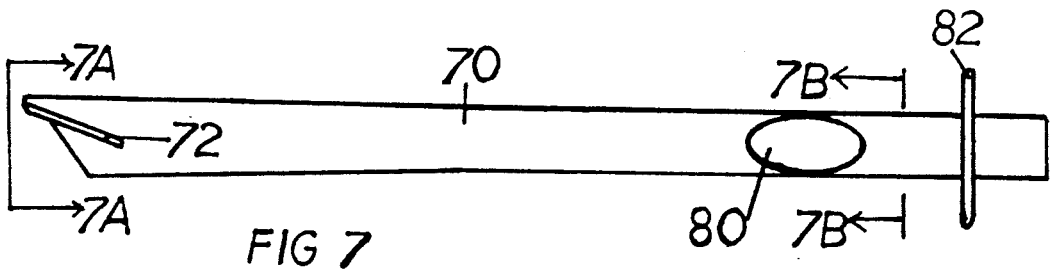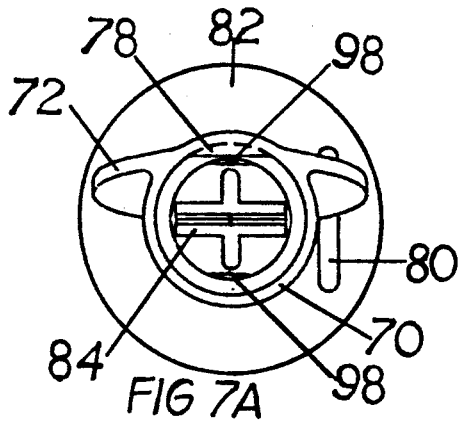

HIGH-VOLUME EJECTOR WITH VALVES AND SPACING FIN

BACKGROUND

Cross-Reference To Related Application

This invention is related and complimentary to the invention of our copending applications, Ser. No. 07/592,360, Filed Oct. 3, 1990, and Ser. No. 07/607,570, Filed Nov. 1, 1990.

BACKGROUND

Field Of Invention

This invention is a dental instrument, specifically a high-volume saliva ejector which in use will reduce microorganism transmission.

BACKGROUND

Prior Art

As indicated in our above-referenced copending applications, despite the precautions and measures taken by dentists to keep their instruments sterile, many of their practices and instruments allow undesired Micro-Organisms (MOs), including viruses, bacteria and fungi, to enter their patients' mouths. These MOs generally come from other patients and are known as cross-contaminants since they travel across from one patient to another. They usually make the inter-patient trip via the air, the dentist's hands, dental instruments, instrument hoses, and instrument holders, as will be shortly discussed. Such cross-contamination was most undesirable in the past because it spread infectious diseases, such as influenza, colds, hepatitis, etc. However it is extremely undesirable now because of its ability to spread the lethal AIDS virus.

In order to understand the modality of cross-contamination, refer to FIG. 1, a side view of typical high-volume saliva and debris suction removal instrument, also known as a high-volume ejector (HVE). If tip 10, holding notch 12, and flange guard 14 are ignored temporarily, the HVE shown is similar to typical prior-art (PA) HVEs. Such HVEs comprise a tube 16 whose proximal (lower) end is connected via a hose valve 18 to a hose 20 and then to a vacuum source (not shown). The distal (upper) end of tube 10 is cut off at an angle as indicated.

During a dental procedure, a dentist or hygienist (hereinafter "DP" for Dental Professional) inserts the HVE into the patient's mouth to suck out saliva and small particles, such as excess filling material, ground-away old fillings and decay, etc. Tube 16 is made of rigid plastic and thus can be directed by the DP to any area of the mouth which needs vacuuming.

During dental procedures, MOs from the patient's mouth accumulate directly on tube 16 and the fingers (not shown) of the DP because the DP inserts such tube and fingers directly into the patient's mouth. Also the DP's fingers and the DP's other instruments accumulate MOs from airborne water mists due to splattering caused when an air-water syringe is used to rinse operative sites and other areas. The DP's fingers also accumulate MOs because they handle tube 16 and other dental instruments, such as scalers, curettes, pliers, etc., which the DP also introduces directly into the mouth.

When the HVE is in the patient's mouth, as stated, a vacuum is applied thereto via hose 20 and valve 18 in order that tube 16 will be able to collect the saliva and debris. However when the HVE is removed, e.g., for the patient and/or DP to rinse, rest, go to the bathroom, etc., the DP and the patient prefer to stop the vacuum since incoming air rushing over the top edge of tube 16 will emit a disturbing and loud unnecessary hissing noise which interferes with conversation. Also tube 16 will suck air from the general room area, causing airborne contaminants to be deposited on the moist tube, where they will remain and possibly infect and contaminate the patient. Thus DPs desire occasionally to stop the vacuum applied to the tube.

To turn off the vacuum, the DP must handle hose valve 18. However by doing this, the DP's MO-laden or contaminated fingers will deposit MOs onto this valve and the hose to which it is connected, thereby contaminating these parts.

When the patient's treatment is completed, the DP will remove and discard tube 16, but will leave the hose and hose valve in place. The hose is too expensive to be replaced for each patient. Since most hose valves are permanently attached to the hose, it too cannot be replaced easily. Replaceable valves are time consuming and difficult to detach and attach to their hoses, so DPs find them undesirable to change for each patient. Furthermore the hose is too sensitive to heat to be autoclaved. While the hose could be chemically sterilized, such a procedure takes about eight hours and requires space, chemicals, valuable time, etc.

When a new HVE is attached for the next patient, the DP will change gloves, wash his or her hands, and insert the HVE in the patient's mouth as before. Thereafter the DP will have to turn off the hose valve periodically, as before. In doing this, the DP will recontaminate his or her fingers by touching the hose and hose valve which were contaminated from the previous patient. Thus when the DP's fingers are inserted into the new patient's mouth, MOs from the previous patient will cross-contaminate the new patient, via the equipment and the DP's fingers. As stated, this cross contamination is very undesirable because it spreads diseases.

Other problems we have noted with prior-art (PA) HVEs are as follows: (1) they tend to dig into and injure patients' gums, i.e., they are traumatic to mucosa, and (2) they are difficult to position accurately since they are difficult to aim and tend to slip off from the teeth, gum, or any other rest place.

OBJECTS AND ADVANTAGES

Accordingly, several objects and advantages are to provide a way to prevent MOs of one patient's mouth from entering other patients' mouths, to reduce the spread of infectious diseases, including AIDS, especially in dentistry, to prevent cross-contamination of patients by MOs, to prevent MOs from cross-contaminating patients via medical instruments, their holders, and/or the fingers of dental personnel, to prevent such cross-contamination with HVEs, to prevent a rushing sound when a HVE is removed from a patient's mouth, to avoid the need to turn off the vacuum source or the hose valve during this operation, to provide HVEs which do not tend to dig into or injure patients' gums, which are easy to position accurately, which provide efficient suctioning in the working field, and which remain more securely upon any rest place.

Other objects are to avoid the need to chemically or thermally sterilize dental fluid hoses and valves, to provide a viable alternative to all non-sterilizable instrument holders, and to provide a HVE valve which is atraumatic to mucosa, patient friendly, less intimidating, and more comforting to patients, and which provides its own screen-filter to prevent suction disposal of good particles.

Further objects and advantages will become apparent from a consideration of the ensuing description and the accompanying drawings.

DRAWING FIGURES

FIG. 1 is a side views of a HVE with a closed integral end valve according to the invention, together with an attached tube, hose valve, flange guard, and hose.

FIG. 2 is a perspective, cutaway view of the end portion of the HVE of FIG. 1. FIG. 2A is a side, partly sectional view of the end portion of FIG. 2. FIGS. 2B and 2C are axial sectional views taken in the direction indicated by the lines 2B—2B and 2C—2C of FIG. 2A.

FIG. 3 is a perspective, cutaway view of the end portion of the HVE of FIG. 1, but with the valve in an open state. FIG. 3A is a side, partly sectional view of the tip of FIG. 3. FIGS. 3B and 3C are axial sectional views taken in the direction indicated by the lines 3B—3B and 3C—3C of FIG. 3A.

FIG. 4 is a perspective, exploded view of an HVE similar to that of FIGS. 1 to 3C, but with a separate (non-integral) valve member.

Figure 5E:
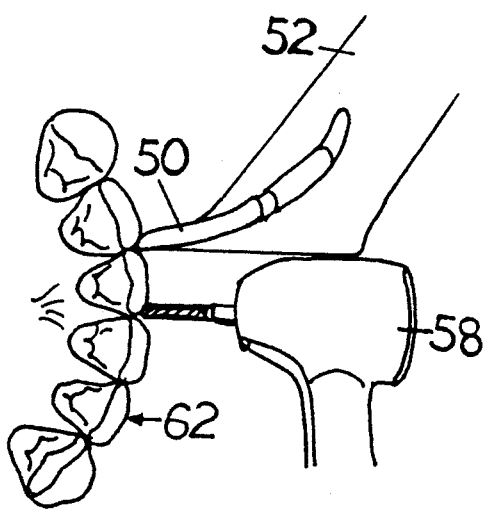
Figure 5F:
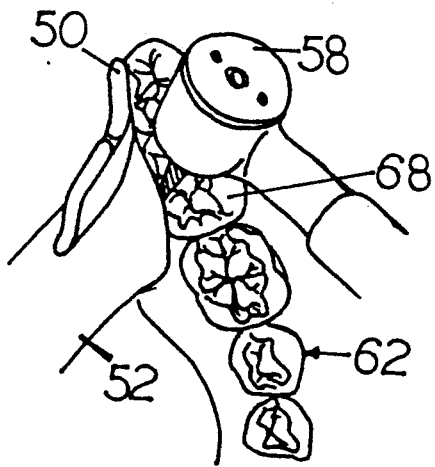

FIG. 5 is a perspective view of a PA HVE tip with a spacer fin. FIGS. 5A to 5C are side, front, and rear views of the HVE of FIG. 5. FIGS. 5D to 5F are perspective and top views of the HVE of FIG. 5 in operation adjacent an incisal and/or facial drilling operation on a tooth on the frontal mandibular arch, adjacent a facial drilling operation on a tooth on the frontal mandibular arch, and adjacent an occlusal and/or lingual drilling operation on a molar or bicuspid tooth on the mandible.

Figure 6D:
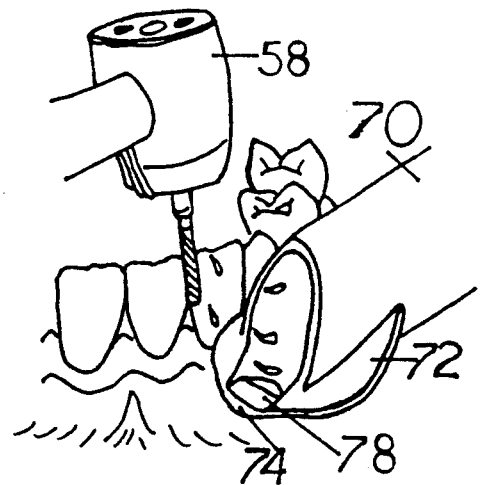
Figure 6E:
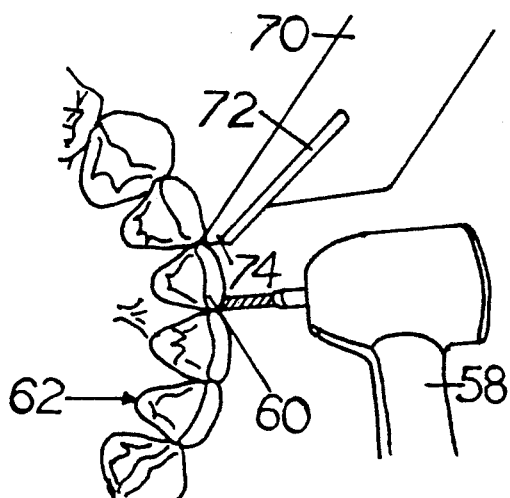
Figure 6F:
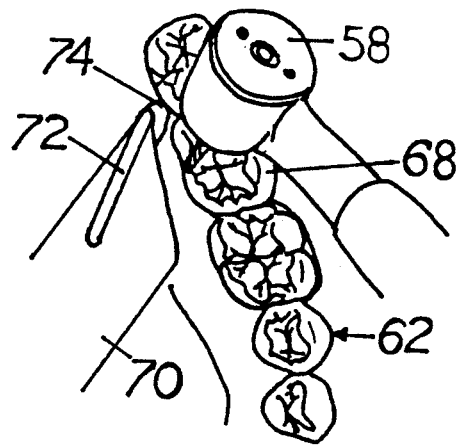

FIGS. 6 to 6F are similar views, but with an HVE with a finned tip according to the invention.

FIG. 7 is a side view of a HVE with a finned tip and an internal valve according to the invention. FIG. 7A is an end view taken in the direction indicated by the line 7A—7A of FIG. 7. FIG. 7B is an axial sectional view taken in the direction indicated by line 7B—7B of FIG. 7. FIG. 7C is a perspective view of a flap valve member in the HVE of FIG. 7. FIGS. 7D and 7E are bottom and side sectional views of the valve of FIG. 7 in an open state, before operation thereof. FIG. 7F is an axial view of the valve of FIG. 7E taken in a direction indicated by the line 7F—7F. FIG. 7G is a side sectional view showing the valve turned to a closed state. FIG. 7H is a bottom view showing the valve returned to an open state after being turned to a closed state.

| Drawing Reference Numerals And Abbreviations | |
|---|---|
| 10 tip | 12 holding notch |
| 14 flange guard | 16 tube |
| 18 hose valve | 18A hose1 |
| 20 hose | 22 flap or disc valve member |
| 24 attachment point | 24A support tabs |
| 26 slot | 28 arm |
| 30 stiffening support | 32 slanted edge |
| 34 slots | 36 pivot hole |
| 38 pintle | 40 stop ball |
| 50 fin | 52 tube |
| 54 bend | 56 notch |
| 58 drill | 60 tooth |
| 62 dental arch | 64 water |
| 66 points | 68 molar or bicuspid |

| -continued | |
|---|---|
| Drawing Reference Numerals And Abbreviations | |
| 70 tube | 72 fin |
| 74 tip | 76 lumen |
| 78 boss | 80 valve handle |
| 82 flange guard | 84 valve |
| 86 plate | 88 pivot arm |
| 90 widened section | 92 widened section |
| 94 fingers | 96 web |
| 98 stop shoulder | |
| HVE high-volume ejector | DP dental professional |
| HDPE high density polyethylene | MO microorganism |
| PA prior art | |

DESCRIPTION

FIGS. 1–3C HVE Ejector with End Valve

In accordance with one aspect of the invention, we provide a high-volume ejector (HVE) with a built-in end valve so that it can be turned off locally by the DP or the patient, thereby avoiding the need to handle the hose valve and hose. The valve is mounted in the tube of the HVE and comprises a flap or disc valve member rotatably mounted in the end of the tube so that it will remain either in a closed position where it is normal to the axis of the tube so as to block same, or in an open position where it is parallel to the axis of the tube where is allows fluid to flow around it.

A perspective, cutaway view of the valved HVE in a closed state is shown in FIG. 2. The HVE comprises the usual tube 16 (preferably made of HDPE—high density polyethylene) attached to a hose1 18A of hose valve 18, which is in turn attached to hose 20. The proximal (lower) end of tube 16 preferably has a flange guard 14 in accordance with the invention of our first copending application above to prevent the DP from inadvertently touching and contaminating the non-disposable parts (valve 18 and hose 20).

In the distal end of tube 16 is a flap or disc valve member 22 which is circular in shape and is attached integrally to the inside surfaces of tube 16 at pivot attachments 24 at opposite sides of the disc. Slots 26 are cut into disc 22 on opposite sides of each attachment 24 so as to form twistable support tabs 24A. The ends of tabs 24A distal from the center of the disc are integral with the side wall of tube 16 and the proximal ends of tabs 24A are integral with the body of the disc. Disc 22 can be rotated 90° on tabs 24A to the open position shown in FIG. 3. HDPE can be molded in this configuration and has sufficient flexibility to provide pivot attachments 24 which are integral and twistable, yet which have enough strength to support disc 22 in either its closed or open positions.

Disc 22 is about 9 mm in diameter and 2 mm thick, slots 26 are about 3 mm deep, and tabs 24A are about 2 mm wide. Tube 16 has an internal diameter of 9.14 mm.

An operating arm 28 about 6 mm long and 2 mm in diameter is molded integrally to the center of disc 22 and extends perpendicularly from disc 22 on the distal side thereof. Arm 28 has a tip 10 which projects out of the distal end of tube 16 (FIGS. 1, 2, and 2A). Another arm 28' extends perpendicularly from the proximal side of disc 22. It is about 3 mm long and about 2 mm in diameter. Arms 28 and 28' and disc 22 form a filter/screen when the valve is in its open (vacuuming) state.

Two stiffening supports 30 are also integrally molded to disc 22 on opposite faces of and in opposite radial positions of disc 22, as best shown in FIGS. 2 and 2A.

Each support is 3.5 mm long, and has a rectangular cross section 1 mm by 1 mm.

Tube 16 is about 203 mm long and its end is cut off at an angle of about 45° to the axis of the tube. The distal end of tube 16 thus forms a curved slanted edge 32. Disc 22 is attached about 11 mm from the distal (remotest) part of edge 32. As shown in FIGS. 1 and 2, a notch 12 is formed in the proximal (nearest) part of edge 32 to receive and hold arm 28. Notch 12 is 2 mm wide by 3 mm deep and is designed to receive tip 10 of arm 28 and hold such tip by slight force fit.

Operation

FIGS. 1–3C

The valved HVE can be supplied and packaged in a package, preferably sterile, in its closed state (FIG. 2). Note that tip 10 of operating arm 28 projects slightly from the end of tube 16 (FIG. 2A) and the edges of disc 22 are adjacent the entire circumference of the inside wall of tube 16. I.e., disc 22 is perpendicular to the axis of tube 16, as best seen in FIG. 2A, so that the disc stops or obturates the lumen of tube 16. Thus no air will flow through tube 16, even if hose valve 18 (FIG. 1) is opened.

To open the HVE valve in order to be able to use it to vacuum a patient's mouth, the DP uses an index finger (not shown) to pull tip 10 of arm 28 down, as indicated by the arrows in FIG. 2A, until it rests in holding notch 12 of tube 16, as indicated in FIG. 3. Due to the force fit between notch 12 and tip 10, tip 10 will remain in this position as long as desired while the HVE is used in the patient's mouth. The tip valve is now open since disc 22 is parallel to the axis of tube 16, as best seen in FIG. 3, thereby providing ample space for air to flow on both sides of disc 22. Disc 22 has rotated 90° on its integral pivot attachments 24.

To close the tip valve, e.g., when removing the HVE from the patient's mouth, the DP or the patient merely pushes tip 10 back to its original position (FIG. 2) where arm 28 is parallel to the tube's axis and disc 22 is perpendicular to such axis. This will cause the HVE to be closed again. The valve will hold this position since disc 22 and its stiffening supports 30 will make a slight force fit with the inside wall of tube 16. Also, the valve will tend to hold its closed position since pivot attachments 24 are in their "home" or untwisted state: they tend to return to this state and resist any change therefrom.

Thus the HVE has a built-in valve so that it can be closed without the DP having to touch any non-sterilizable or difficult-to-sterilize hose valve or shut off the vacuum when the HVE is removed from a patient's mouth. This will aid in preventing MOs from travelling between patients' mouths, thereby reducing the spread of infectious diseases, including AIDS.

DESCRIPTION

FIG. 4

Saliva Ejector With Non-Integral Tip Valve

In lieu of making the tip valve integral with the tube (FIG. 2), it can be made separate, as shown in FIG. 4. In FIG. 4, tube 16' has a pair of slots 34 on opposite sides thereof which extend in from edge 32' about 5 mm. At the end of each slot is a widened, circular pivot hole 36. Disc 22' is similar to that of FIG. 2, except that in lieu of integral pivot attachments, a pair of pintles or pivot arms 38 extend from opposite edges of the disc. Each pintle is about 2 mm long and has a stop ball 40 at its end. Disc 22' is mated with tube 16', as indicated by the projection line, by bringing the two components together until pintles 38 slide into slots 34, respectively, and disc 22' slides into tube 16'. The assembler further moves the disc into the tube until pintles 38 rest in pivot holes 36, respectively. The disc is now completely assembled into the tube and the resultant assembly (not shown) will appear as in FIG. 2, except that in lieu of integral pivot attachments 24, it will be retained by pintles 38 resting in holes 36. The non-integrally valved HVE is sold and packaged in this manner. Its operation is virtually identical to the integrally valved HVE of FIG. 2. The device of FIG. 4 can be molded more easily.

FIGS. 5–5F

Prior-Art HVE With Finned Tip

The PA HVE tube of FIGS. 5 to 5C is similar to that of FIG. 1, except that the tip valve and flange guard are omitted, and a spacing fin 50 is integrally molded to extend out from opposite sides and the end of the tube, here designated 52. Fin 50 has a generally square shape (FIGS. 5B and 5C), has a curve 54 near its lower end, merges with the slant of the tube at its distal or upper end, and has a pair of notches at about the midpoints of each its sides.

The purpose of fin 50 is to spread the patient's cheek away from the teeth so that the vacuum in tube 52 will not suck the patient's cheek, which is flexible and floppy, over the open end of tube 52. However when the PA HVE of FIG. 5 is used, it has a number of disadvantages.

FIG. 5D is a perspective view of the HVE of FIG. 5 in operation. A drill 58 is being used for an incisal and/or facial drilling operation on a tooth 60 on a frontal mandibular arch 62. A PA HVE tube 52 with fin 50 is placed between arch 62 and the patient's cheek (not shown) to suck away water sprayed from drill 58 and debris (not shown) from the drilling operation. However we have noted that fin 50 has two front points 66 which dig into the patient's gum and cheek, resulting in additional pain and discomfort during the drilling operation. Also the flat front end of fin 50 between points 66 makes it difficult to aim the HVE and position it accurately. Further, the HVE slips up and down on the surface of the tooth and gum. In addition, the open end of the HVE cannot be brought very close to the drilling site because of the space taken by the square front end of the fin, thereby reducing the efficiency of the vacuuming operation. The coalesced water droplets from spray on fin 50 between points 66 tend to drip away from the tube lumen because of the severe angle (about 45° between the fin and the long axis of tube 52.

FIG. 5E is a top view of the PA HVE tube 52 in operation adjacent drill 58 in use for a facial and/or interproximal drilling operation on a tooth 60 on arch 62. Note that for its open end to be placed close to the drill, the HVE must actually be placed very close to or in contact with the drill, thereby interfering with the dentist's freedom to manipulate the drill. In addition, all of the disadvantages noted in the previous paragraph are still present.

FIG. 5F is a perspective view of the PA HVE in operation adjacent to drill 58 in use for an occlusal and/or lingual drilling operation on a molar or bicuspid tooth 68 on the mandible (lower jaw). Note that the open end of tube 52 is placed adjacent the tooth, thereby obscuring the side of the tooth and making the dentist's task more difficult and very dangerous. It is difficult and tiring for the dentist to hold the open end away from the tooth as there is no place to rest or to hold the open end. Again, all of the disadvantages noted in the previous paragraphs are still obtained.

FIGS. 6-6F

HVE With Finned Tip

According to the invention, the difficulties with the PA finned HVE of FIG. 5 are overcome with a finned tip of the invention as shown in FIGS. 6 to 6F, which correspond to FIGS. 5 to 5F.

In accordance with the invention, an HVE tube 70 has a round or generally circular fin 72 with a somewhat pointed front or distal end 74. Instead of curving and merging with the angle of the open end of the tube (FIG. 5A), fin 72 is straight and extends in front of the slanted open and at a narrower angle to the tube's axis, as shown in FIG. 6A. Although fin 72 has been described as circular with a somewhat pointed front end, it is open or interrupted in its center portion so as not to block the open lumen 76 of tube 70. As shown in FIG. 6C, fin 72 does not extend behind or block the back surface of tube 70. As shown in FIGS. 6 to 6B, the upper portion of lumen 76 has a raised boss, nubbin, or projecting bulge 78 to make pointed end 74 less sharp so as to decrease trauma to the gum and cheek. The fin projects beyond the open distal end of the tube (FIG. 6A) so that said fin intersects the open distal end when seen from a direction coplanar with the fin. Also, when seen from this direction, the fin is confined between the outside surfaces of the side wall of the tube.

The advantages of the fin of the invention can best be seen in FIGS. 6D to 6F. In FIG. 6D tube 70 with fin 72 is placed between arch 62 and the patient's cheek (not shown) to suck away water sprayed from drill 58 and debris from the drilling operation. Since fin 72 has no front points, it will not dig into the patient's gum and cheek, resulting in a far more atraumatic procedure and less pain and discomfort during the drilling operation. Also round point 74 and nubbin 78 makes it easy to aim the HVE and position it accurately. Further, due to point 74, the HVE has far less tendency to slip up or down on the surface of the tooth and gum. In addition, the open end of the HVE can be brought closer to the drilling site because no space is taken by any square front end of the fin, thereby increasing the efficiency of the vacuuming operation.

FIG. 6E is a top view of the HVE in operation adjacent drill 58 in use for a facial drilling operation on tooth 60 on arch 62. Note that tip 74 of tube 70 can be placed close to the drill (thereby to obtain efficient vacuuming) without placing the rest of the open end close to or in contact with the drill. This greatly reduces interference and allows the dentist far more freedom to manipulate the drill. In addition, all of the disadvantages noted in the previous paragraph are greatly reduced or eliminated.

FIG. 6F is a perspective view of the HVE in operation adjacent drill 58 in use for an occlusal and/or lingual drilling operation on a molar or bicuspid tooth 68 on the mandible. Note that tip 74 again can be placed adjacent the tooth and drill (thereby to obtain efficient vacuuming) without placing the rest of the open end of tube 70 adjacent the tooth (thereby freeing the side of the tooth for visibility and safety and making the dentist's task much easier). It is now easy for the dentist to hold the open end away from the tooth as point 74 provides a place which can be rested or positioned against tooth or gum. Again, all of the disadvantages noted in the previous paragraphs are also greatly reduced or eliminated.

FIGS. 7-7H

HVE With Finned Tip And Internal Valve

Figure 7D:
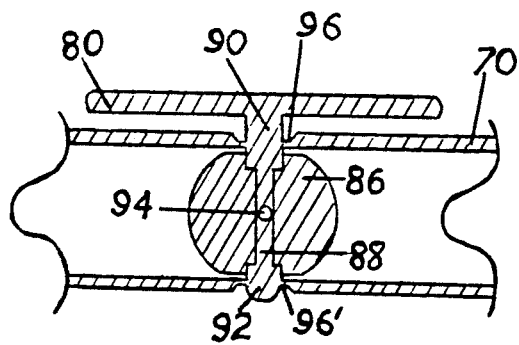

While the tip valve of FIG. 2 can be provided on the HVE of FIG. 6, some DPs will prefer to be able to open or close the valve with the hand that holds the HVE. To accomplish this, we have provided a valve at an intermediate location on this HVE, as shown in FIGS. 7 to 7H.

FIG. 7 shows a side view of the entire HVE. The HVE has a tube 70 and fin 72, as in FIG. 6, a valve operating handle 80 (generally elliptical for directionality of shape) connected to an internal valve (shown in FIGS. 7A to 7H), and a flange guard 82, which comprises a disc attached near the proximal end of the valve to deter the DP from touching any non-sterilizable parts, as described in more detail in our above copending '360 application.

An end or axial view of the HVE is shown in FIG. 7A. Note that flange 82 is more than twice the diameter of tube 70. Also note how fin 72 and boss 78 are positioned on the tube. Handle 80 is on the outside of the tube, between fin 72 and flange 82. Handle 80 is connected to and operates a flap valve 84 inside the tube; valve 84 is shown in its open or transmissive state. FIG. 7B shows a sectional view of the HVE from the opposite direction; note that in this view, handle 80 is in front of fin 72. Tube 70 is wider at its distal end (15 mm outside diameter) than at its proximal end (10.92 mm), thus resulting in two circumference lines in FIGS. 7A and 7B.

Figure 7C:
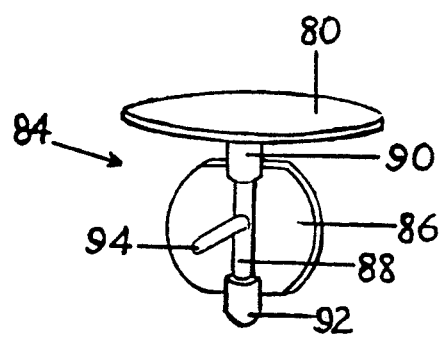
Figure 7E:
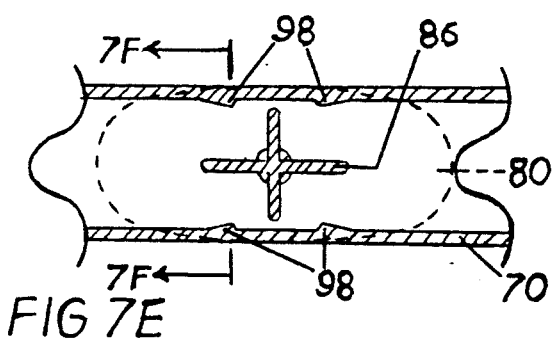
Figure 7F:
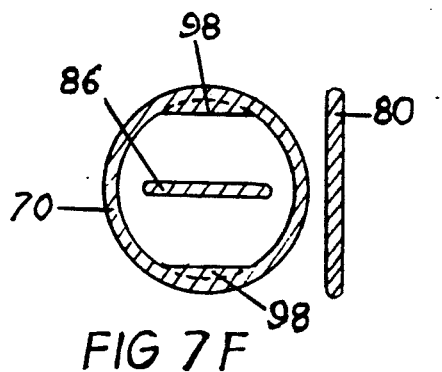
Figure 7G:
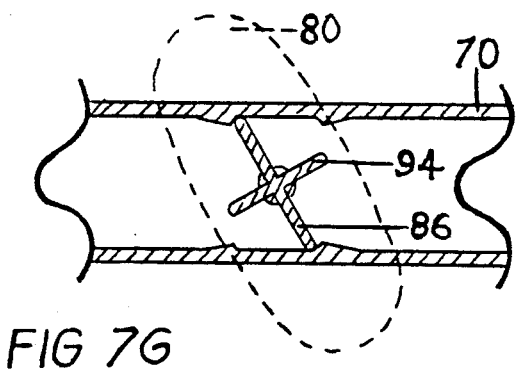
Figure 7H:
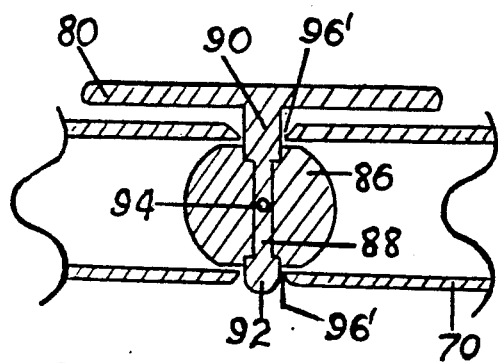

As shown in the perspective view of FIG. 7C, valve 84 comprises a flat plate 86 which has two curved opposite sides and two intermediate, opposite flat sides. Plate 86 is mounted on a pivot arm 88, the upper end of which (in FIG. 7C) is attached to handle 80 by a widened section 90 which extends through the wall of tube 70, as will be described. The other end of arm 88 is another widened section 92 which is pivotably mounted in the opposite side of the wall of tube 70, as will be described. In operation, the DP turns handle 80 to cause plate 86 to be either parallel to the axis of the tube so that the lumen of the tube is patent or open (FIGS. 7A, 7B, 7D, 7E, 7F, and 7H), or normal to the axis of the tube so that the lumen of the tube is obturated or closed (FIGS. 7G).

A pair of fingers 94 are attached to arm 88 and are normal to the arm and to plate 86. As shown in FIGS. 7E and 7G, fingers 94 are shorter than the sides of plate 86 and both are much smaller than handle 80. Fingers 94 are part of a cruciform filter screen which is formed by fingers 94 and plate 86 in the open state. The filter is used to trap useable particles (crowns, inlays, etc.) from being sucked further down the contaminated hose.

FIGS. 7D and 7E are bottom and side sectional views of the valve of FIG. 7 in an open state, as supplied by the manufacturer and before operation thereof. Note from FIG. 7D that widened section 90 is integrally attached to the wall of tube 70 by a thin circumferential web 96. Also widened section 92 is attached to the opposite side of the tube's wall by another thin circumferential web 96'. Each of widened portions 90 and 92 are 2.54 mm in diameter and the surrounding webs are 300 um (microns) thick. All other parts are sized proportionately. The entire assembly consisting of tube 70, handle 80, valve 84, fin 72, and flange 82 is integrally molded in one piece and in one operation using a two-piece exterior mold to form the tube and the external parts. Two plug inserts which are pulled out in opposite directions are used to form the valve inside the tube.

Note from FIG. 7E that the lumen of tube 70 is open or patent since plate 86 is parallel to the tube's axis. Also note that the side wall of tube 70 has a two pairs of stop shoulders 98 on opposite sides, intermediate webs 96. Each shoulder consists of a raised ledge which is designed to mate with the edge of plate 86 when it is turned to be almost normal to the tube's axis, as shown in FIG. 7G. In use, the DP can use the HVE immediately after connecting it to a vacuum hose since it comes with valve 84 in an open state.

When the DP desires to close the valve in order to prevent the rushing sound, e.g., after removing it from the patient's mouth, the DP can do so simply by turning handle 80 in either direction about 70°, as shown in FIG. 7G. This will rupture webs 96 (which are thin and thus frangible) on both sides of pivot arm 88, leaving widened sections 90 and 92 extending through holes in the wall of tube 70, as shown in FIG. 7H at 96'. When the DP turns handle 80 in this manner, plate 86 will block or obturate the lumen of tube 70, as shown in FIG. 7G. This will prevent any air from flowing through tube 70 and thus the rushing sound will cease. The valve will remain in this off or closed state as long as desired because plate 86 is physically held in place by stops 98 and the wall of the tube.

To re-open the valve, the DP simply returns handle 80 to its open position (FIGS. 7E, 7F) where it is parallel to the tube. When the valve is so returned to its open state, it will be as shown in FIG. 7H; this Fig is identical to FIG. 7D, except that the webs have been replaced by holes 96'. The valve will remain in this on or open state as long as desired because the valve handle is held within the DP's palm and the major axis of the elliptically shaped valve handle is parallel to tube 70. Thus the periphery of the handle stays within the outer diameter of tube 70. Incoming air hitting plate 86 also tends to keep the valve open initially.

SUMMARY, RAMIFICATIONS, AND SCOPE

The reader will thus see that we have provided a saliva ejector with built-in valves which enable the HVE itself to be closed. Thus the DP does not have to touch the non-sterilizable or difficult-to-sterilize hose valve or shut off the vacuum when the HVE is removed from a patient's mouth. This will aid in preventing MOs from travelling between patients' mouths, thereby reducing the spread of infectious diseases, including AIDS. The HVE can be made economically, it is reliable and easy to use, it is simple and safe in operation, and it is very comfortable.

In the finned version, the HVE is easy to aim and position, is comfortable and atraumatic to the patient's tissues, is easy to retain in position, and does not interfere with the drill or other dental instrument or tooth. Also, the finned HVE can still be turned off by its own valve without having to touch any non-sterilizable parts. Both versions can have the valve with its inherent screen-filter.

While the foregoing description and accompanying drawing contain many specificities, these should not be considered as limitations on the invention since many variations are possible within its scope. For example the HVE can be made of other materials than as indicated. The valves are not limited to dental use, but can be used for other applications, such as siphon tube valves, general suction pump hose valves, etc. The valves can be used to close of an outflow of fluid, rather than an inflow, in which case the tube should be connected to a source of fluid pressure which is higher, rather than lower, than the ambient pressure outside the valve. The valves can be sold separately from the tube so that the user can install either one on any tube, preferably by cementation, but also by friction or snap fit, either to the end of the tube, or by splicing it within a length of tube. The handle of FIG. 7 can have shapes other than elliptical.

Accordingly the full scope of the invention should be determined by the appended claims and their legal equivalents, and not by the examples given.

We claim:

1. A valved tube comprising:
   a tube having a cylindrical side wall, said side wall having outside and inside surfaces, said tube having a lumen surrounded by said inside surface of said side wall, said tube having an open distal end and an imaginary longitudinal axis through said lumen, said axis being parallel to said lumen and said side wall of said tube,
   a valve comprising a plate,
   pivot means for pivotably mounting said plate within said lumen and adjacent said open distal end of said tube,
   said plate having a size and shape such that when said plate is perpendicular to said longitudinal axis, said plate will be in an obturating position which substantially occludes said lumen,
   said pivot means mounting said plate within said lumen such that said plate can be pivoted from said obturating position to an open position in which said plate is parallel to said longitudinal axis, and thereafter back to said obturating position,
   operating means for enabling a person to move said plate between said obturating and said open positions from outside said tube, said operating means comprising a member having proximal and distal opposite ends, said proximal end being rigidly attached to said plate, said distal end of said member projecting out said distal end of said tube such that said person can pivot said distal end of said member with a finger from outside said tube and thereby pivot said plate from said obturating position to said open position, and
   obturating position holding means for holding said plate in said obturating position when said plate is moved to said obturating position so that said plate will resist movement thereof away from said obturating position, and
   open position holding means for holding said plate in said open position when said plate is moved to said open position so that said plate will resist movement thereof away from said open position.

2. The valved tube of claim 1 wherein said pivot means comprises a pair of twistable attachments connecting opposite edges of said plate to said inside surface of said tube.

3. The valved tube of claim 2 wherein said pair of twistable attachments are integrally connected to said inside surface of said tube.

4. The valved tube of claim 1 wherein said pivot means comprises a pair of pintles connected to opposite edges of said plate and extending through respective pivot holes in said side wall of said tube.

5. The valved tube of claim 1 wherein said open position holding means comprises a notch in said distal end of said tube, said notch being positioned and shaped to receive and frictionally engage said member when said plate is moved to said open position.

6. The valved tube of claim 1 wherein said obturating position holding means comprises an edge of said plate which is shaped to frictionally engage said inside surface of said tube when said plate is moved to said obturating position.

7. The valved tube of claim 1, further including another member extending from said plate on the side thereof opposite to said first-named member, said another member extending normal to and from said plate.

8. The valved tube of claim 1 wherein said pivot means comprises a shaft extending across said plate and means for journalling opposite ends of said shaft within opposite portions of said side wall, and wherein said plate lies in a plane which is oblique to said axis of said tube.

9. The valved tube of claim 1 wherein said open position holding means comprises a notch in said distal end of said tube, said notch being positioned and shaped to receive and frictionally engage said member when said plate is moved to said open position, and wherein said obturating position holding means comprises an edge of said plate which is shaped to frictionally engage said inside surface of said tube when said plate is moved to said obturating position.

10. The valved tube of claim 9 wherein said pivot means comprises a pair of twistable attachments connecting opposite edges of said plate to said inside surface of said tube, said pair of twistable attachments being integrally connected to said inside surface of said tube.

11. The valved tube of claim 9 wherein said pivot means comprises a pair of pintles connected to opposite edges of said plate and extending through respective pivot holes in said side wall of said tube.

12. The valved tube of claim 1 wherein said open distal end of said tube is generally oblique to said axis of said tube.

13. A valve for use within a tube for closing off an opening in said tube, comprising:
a tubular housing having an encircling side wall, said side wall having outside and inside surfaces, said housing having a lumen therewithin, said housing having an open distal end and an imaginary longitudinal axis through said lumen,
a valve comprising a plate having a size and shape such that when said plate is in an obturating position within said lumen perpendicular to said longitudinal axis, said plate will substantially occlude said lumen,
pivot means for pivotably mounting said plate within said lumen such that said plate can be pivoted from said obturating position to an open position parallel to said longitudinal axis, and back to said obturating position, and
operating means comprising a handle for enabling a person to move said plate between said obturating and said open positions from outside said tube,
said pivot means comprising a shaft which is integrally joined to said wall of said tube between said plate and said handle by a frangible web.

14. The valved tube of claim 13 wherein said handle is outside said tube, one end of said shaft being connected to said handle through said wall of said tube.

15. The valved tube of claim 14 wherein both ends of said shaft are integrally joined to said opposite portions of said side wall by respective frangible webs.

16. A dental saliva ejector of the type comprising a tubular housing having an encircling side wall, said side wall having outside and inside surfaces, said housing having a lumen therewithin, said housing having an open distal end and an imaginary longitudinal axis through said lumen, said open distal end being slanted with respect to said axis, and a flat spacing fin attached to and projecting from opposite sides of said outside surface adjacent said distal end, an improvement wherein said fin is oriented at a smaller angle to said axis than said open distal end, and said fin projects beyond said open distal end so that said fin intersects said open distal end when seen from a direction coplanar with said fin.

17. The dental saliva ejector of claim 16 wherein said fin has a shape, when seen from a direction normal thereto, which is generally circular and free from corners.

18. The dental saliva ejector of claim 16 wherein said fin has a shape, when seen from a direction coplanar with said fin, which is confined between said outside surfaces of said side wall of said tube.

19. The dental saliva ejector of claim 16 wherein said tubular housing includes:
a valve comprising a plate having a size and shape such that when said plate is in an obturating position within said lumen perpendicular to said longitudinal axis, said plate will substantially occlude said lumen,
pivot means for pivotably mounting said plate within said lumen such that said plate can be pivoted from said obturating position to an open position parallel to said longitudinal axis, and back to said obturating position, and
operating means for enabling a person to move said plate between said obturating and said open positions from outside said tube.

20. The dental saliva ejector of claim 19 wherein said operating means comprises a member having proximal and distal opposite ends, said proximal end being attached to said plate, said distal end of said member projecting out said distal end of said tube.

* * * * *